United States Patent
Bigler et al.

(10) Patent No.: US 8,178,094 B2
(45) Date of Patent: May 15, 2012

(54) METHODS FOR INHIBITING TUMOR GROWTH OR REDUCING METASTATIC BURDEN IN A SUBJECT BY ADMINISTERING FDF03 ANTIBODIES

(75) Inventors: Michael E. Bigler, Redwood City, CA (US); Drake M. LaFace, Half Moon Bay, CA (US); Kalyan Pande, San Francisco, CA (US); Joseph H. Phillips, Palo Alto, CA (US)

(73) Assignee: Schering Corporation, Rayway, NJ (US)

( * ) Notice: Subject to any disclaimer, the term of this patent is extended or adjusted under 35 U.S.C. 154(b) by 0 days.

(21) Appl. No.: 12/809,554

(22) PCT Filed: Dec. 18, 2008

(86) PCT No.: PCT/US2008/087371
§ 371 (c)(1),
(2), (4) Date: Jun. 29, 2011

(87) PCT Pub. No.: WO2009/085920
PCT Pub. Date: Jul. 9, 2009

(65) Prior Publication Data
US 2011/0256143 A1    Oct. 20, 2011

Related U.S. Application Data

(60) Provisional application No. 61/015,548, filed on Dec. 20, 2007.

(51) Int. Cl.
*A61K 39/395* (2006.01)
*A61K 39/00* (2006.01)

(52) U.S. Cl. ................ 424/130.1; 424/133.1; 424/136.1

(58) Field of Classification Search ........................ None
See application file for complete search history.

(56) References Cited

U.S. PATENT DOCUMENTS

| 6,140,076 A | 10/2000 | Adema et al. |
| 6,774,214 B1 | 8/2004 | Bates et al. |
| 2005/0287582 A1 | 12/2005 | Adema et al. |

FOREIGN PATENT DOCUMENTS

| WO | WO 03/030835 | 4/2003 |
| WO | WO 2007/099921 | 9/2007 |

OTHER PUBLICATIONS

Banerjee et al., (2010) *Infec. Immunity* 78(3):1353-1363 "Modulation of paired immunoglobulin-like Type 2 receptor signaling alters the host response to *Staphylococcus aureaus*-induced Pneumonia".
Fournier et al. (2000) *J. Immunol.* 165(3):1197-1209 "FDF03, a novel inhibitory receptor of the immunoglobulin superfamily, is expressed by human dendritic and myeloid cells".
Mousseau et al. (2000) *J. Biol. Chemistry* 275(6):4467-4474 "PILRalpha, a novel immunoreceptor tyrosine-based inhibitory motif-bearing protein, recruits SHP-1 upon tyrosine phosphorylation and is paired with the truncated counterpart PILRbeta".
Satoh, et al. (2008) *Cell* 132(6):935-944 "PILRalpha is a herpes simplex virus-1 entry coreceptor that associates with glycoprotein B".
Scotlandi et al. (2006) *Eur. J. Cancer* 42(1):91-96 "Targeting CD99 in association with doxorubicin: An effective combined treatment for Ewing's sarcoma".
Shiratori et al. (2004) *J. Exp. Med.* 199(4):525-533 "Activation of Natural Killer Cells and Dendritic Cells upon Recognition of a Novel CD99-like Ligand by Paired Immunoglobulin-like Type 2 Receptor".

*Primary Examiner* — Robert Landsman
(74) *Attorney, Agent, or Firm* — Gregory R. Bellomy

(57) ABSTRACT

The present invention relates to methods for identifying and using modulators of FDF03 biological activity in vitro and in vivo that are useful in the treatment of cancer.

14 Claims, 5 Drawing Sheets

METHODS FOR INHIBITING TUMOR GROWTH OR REDUCING METASTATIC BURDEN IN A SUBJECT BY ADMINISTERING FDF03 ANTIBODIES

FIELD OF THE INVENTION

The present invention relates to the fields of immunology and medicine. More particularly, the invention relates to the modulation of FDF03 activity to enhance antitumor activity in vivo, and identification of compounds that mediate such modulation.

BACKGROUND OF THE INVENTION

The activation threshold of immune cells is regulated by activating and inhibitory signals received through recognition of self and foreign antigens. Genetic defects that affect activating or inhibitory receptors renders the immune system unable to distinguish between self and non self causing autoimmunity or abnormal response against infectious agents and transformed cells (see, e.g., Walker and Abbas (2002) *Nat Rev Immunol.* 2:11-19; and Lanier (2003) *Curr Opin Immunol.* 15:308-314).

Cells of the immune system possess many types of membrane-bound proteins that serve as receptors. The ligands for these receptors may be small molecules, proteins, e.g., cytokines or chemokines, or membrane-bound proteins residing on a separate cell. The occupation of a receptor by its ligand, binding of a receptor by a soluble antibody, cross-linking of like-receptors to each other, and cross-linking of unlike receptors to each other, can result in changes in cellular activity. Some of these events result in "cell activation," while other events result in "cell inhibition."

Studies of immune cells and their activation or inhibition have related to: Recruitment of enzymes to the plasma membrane; recruitment of enzymes to "lipid rafts" in the cell membrane (Yang and Reinherz, *J. Biol. Chem.* 2766, 18775 (2001)), and recruitment of membrane-bound receptors to the plasma membrane. A lipid raft is a region of the plasma membrane with reduced fluidity of the lipid molecules. Cell activation or inhibition also relates to changes in phosphorylation state of receptors; changes in the proliferative state of the cell; calcium fluxes; changes in genetic expression; changes in secretion or in degranulation; differentiation of the cell; changes in the proliferative rate of the cell; changes in cell migration; and changes in chemotaxis. Cell activation may also include the reversal of T cell anergy (see, e.g., Lin, et al., *J. Biol. Chem.* 273, 19914 (1998); and Sunder-Plassman and Reinherz, *J. Biol. Chem.* 273, 24249 (1998)).

The question of whether a signaling event, which results in any of the above changes, is activating or inhibiting can be determined on an individual basis. For example, if occupation of an unidentified receptor results in an increases of genetic expression of cytokine mRNA, secretion (or degranulation), release of inflammatory cytokines, phagocytic or lytic activity, the unidentified receptor may be termed an activating receptor. Similarly, if occupation of an unidentified receptor inhibits activity dependent on a known activating receptor, then that unidentified receptor may be termed an inhibiting receptor.

The determination of whether a receptor is activating or inhibiting may be predicted by the polypeptide sequence of the receptor, where the receptor is a protein. Attention has focused on two different motifs: ITIM and ITAM. ITIM stands for immunoreceptor tyrosine-based inhibition motif, while ITAM means immunoreceptor tyrosine-based activation motif. A number of polypeptide receptors bearing one or more ITIM motifs in the cytosolic region of the receptor have been found to be inhibiting, whereas a number of polypeptide receptors bearing one or more ITAM sequences in the cytosolic region have been found to be activating.

Recently, a number of such immunoregulatory receptors like TREMs, MDL-1, FDF03, DCIR, and CD200 have been identified on myeloid cells. FDF03 is also known as Paired Immunoglobulin-Like type 2 Receptor (PILR). The PILR family comprises both inhibitory (PILRα) and activating (PILRβ) isoforms. Both receptors belong to the v-type immunoglobulin superfamily and are expressed on the surface of neutrophils, monocytes, and dendritic cells. PILRb is also present on NK cells and a small population of T cells in both the mouse and human (see, e.g., Shiratori, et al. (2004) *J Exp Med.* 199:525-33). PIRLα possesses an ITIM in its cytoplasmic domain, whereas the PILRβ transduces activating signals by associating with the ITAM-bearing DAP12 adaptor molecule. The putative ligand for the mouse isoforms was identified to be a CD99-like molecule and more recently, it was observed that the O-glycan sugar chain on CD99 was involved in receptor recognition. Earlier studies in DCs and macrophages have indicated that PILRα can inhibit ITAM-mediated activation signals, a feature common among the ITIM-bearing family of receptors. PILRα exhibited an inhibitory role by blocking intracellular Ca+2 mobilization induced by CD32/FcγRII in FDF03 transfected U937 cells. PILRα has also been identified as a herpes-simplex virus-1 entry co-receptor (see, e.g, Satoh, et al. (2008) *Cell* 132:935-944.

Innate immunity is distinguished from adaptive immunity in that innate immune cells do not require prior exposure to a particular microbial pathogen or tumor associated antigen to be induced to respond vigorously. In addition, the receptors utilized by innate immune cells are non-polymorphic and generally recognize specific molecular patterns present on microbial pathogens. Thus, innate immune cells provide a first line of defense against pathogens. Typically, an innate immune response is mediated through various myeloid lineage cells, as a first line of defense to pathogens and cancers. Myeloid lineage cells include macrophages, monocytes, dendritic cells, neutrophils, eosinophils, granulocytes, mast cells, basophils, etc. In addition, NK cells are part of innate immunity as well as they express non-polymorphic receptors capable of recognizing altered self; particularly cells that lack MHC class I expression as is the case for many tumor cells. As noted above, FDF03 receptors are expressed on the surface of myeloid lineage cells. In addition, the activating form of FDF03 can be expressed on NK cells. Recent research has explored the concept that innate immune cells may distinguish on microbial pathogen or tumor cell target by processing signal transductions derived from multiple non-polymorphic receptors. Thus one pathogen may trigger receptor interactions based on the various molecules expressed and another pathogen may trigger a different array of receptors, thus triggering differential responses in a qualitative or quantitative manner. Thus, triggering combinations of receptors on innate cells with a combination therapy using two or more agonist molecules may augment the capacity to induce pathogen clearance or tumor cell killing.

A need exists for regulators of immunity, in particular cancer immunity. The present invention fulfills this need by providing methods of regulating cancer immunity with modulators of FDF03 receptors.

BRIEF SUMMARY OF THE INVENTION

The present invention is based upon the discovery that modulation of FDF03 activating (PILRβ) and inhibiting (PILRα) receptors, cell surface molecules on hematopoietic cells, can change the dynamics of an ongoing immune response or the initiation of a primary immune response to a tumor or cancer, or inhibiting metastasis. Thus receptors can be significant targets for modulating of immune responses in vivo.

The present invention provides a method for inhibiting tumor growth in a subject, comprising administering to a subject in need thereof an agent that stimulates or enhances FDF03 inhibitory receptor biological activity. In certain embodiments, the agent is an agonist or partial agonist antibody or antibody fragment thereof specific for the FDF03 inhibitory receptor; the antibody can be a humanized, fully human or chimeric antibody; the tumor is a primary or a metastatic tumor; or the subject is a human.

Also provided is a method for reducing metastatic burden in a subject comprising administering to a subject in need thereof an agent that stimulates or enhances FDF03 inhibitory receptor biological activity. In certain embodiments agent is an agonist or partial agonist antibody or antibody fragment thereof specific for the FDF03 inhibitory receptor; the antibody is a humanized, fully human or chimeric antibody; or the subject is a human.

The present invention provides a method for inhibiting tumor growth in a subject, comprising administering to a subject in need thereof an agent that binds to both FDF03 inhibitory and FDF03 activating receptors. In certain embodiments, the agent is a bispecific antibody or antibody fragment thereof that binds to the FDF03 inhibitory receptor and the FDF03 activating receptor; the antibody is a humanized, fully human or chimeric antibody; the tumor is a primary or a metastatic tumor; or the subject is a human.

Also provided is a method for reducing metastatic burden, comprising administering to a subject in need thereof an agent that binds to both FDF03 inhibitory and FDF03 activating receptors. In certain embodiments, the agent is a bispecific antibody or antibody fragment thereof that binds to the FDF03 inhibitory receptor and the FDF03 activating receptor; the antibody is a humanized, fully human or chimeric antibody; or the subject is a human.

DETAILED DESCRIPTION OF THE INVENTION

Figure 1:
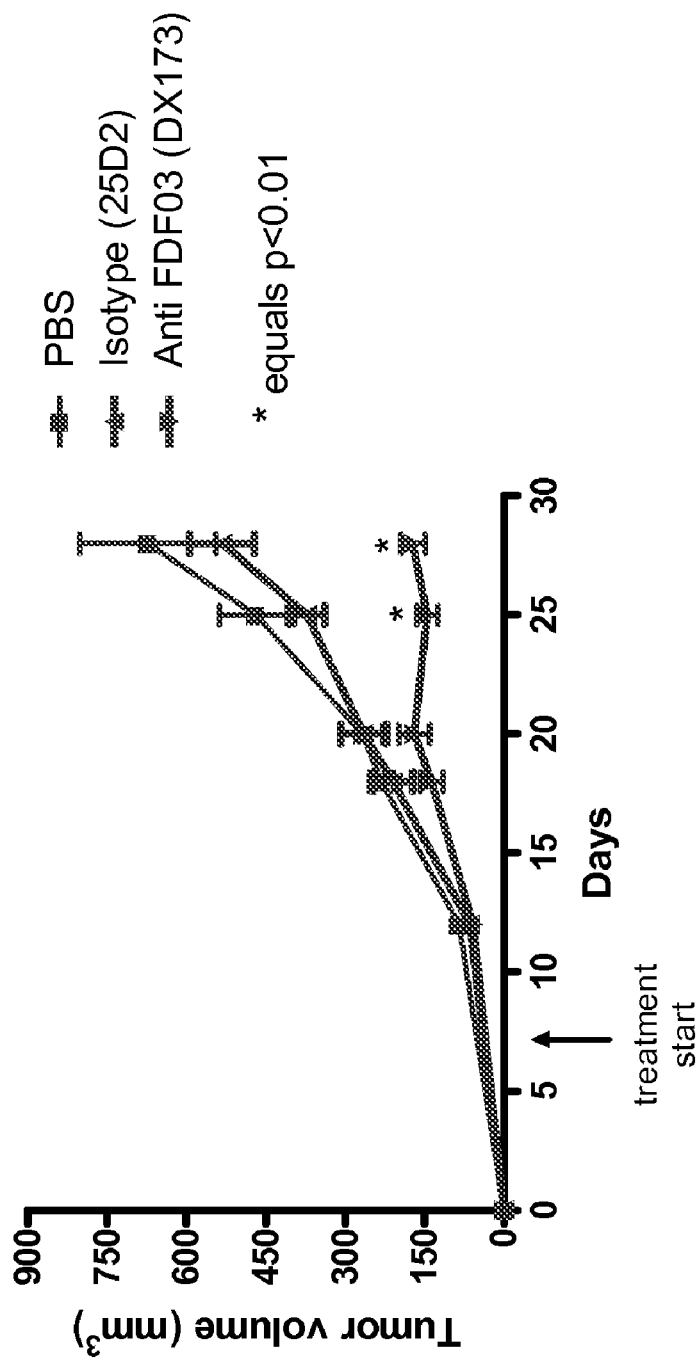
FIG. 1 shows inhibition of 4T1 mammary carcinoma tumor growth upon treatment with DX173 (bispecific antibody that binds to FDF03 activating and FDF03 inhibitory receptors) antibodies.

The present invention relates to the physiological role for FDF03 receptors as a critical regulator of immune responses. In a mouse model, agonizing the inhibitory form of the FDF03 receptor results in an augmentation of anti-tumor immune responsiveness both to primary tumor outgrowth as well as a reduction in metastatic burden, implicating FDF03 as an important player in immunosurveillance. Thus, the object of the present invention relates to the modulation of FDF03 to alter immune responsiveness, particularly in cancer. The ability to identify agents that modulate FDF03 receptors permits the external regulation of immune response and may permit the enhancement of tumor immunosurveillance to at least reduce, if not prevent carcinogenesis and tumor growth.

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, published patent applications and other publications and sequences from GenBank and other databases referred to herein are incorporated by reference in their entirety. If a definition set forth in this section is contrary to or otherwise inconsistent with a definition set forth in patents, published patent applications and other publications and sequences from GenBank and other data bases that are herein incorporated by reference, the definition set forth in this section prevails over the definition that is incorporated herein by reference.

As used herein, "a" or "an" means "at least one" or "one or more."

"Administration" and "treatment," as it applies to an animal, human, experimental subject, cell, tissue, organ, or biological fluid, refers to contact of an exogenous pharmaceutical, therapeutic, diagnostic agent, compound, or composition to the animal, human, subject, cell, tissue, organ, or biological fluid. "Administration" and "treatment" can refer, e.g., to therapeutic, placebo, pharmacokinetic, diagnostic, research, and experimental methods. "Treatment of a cell" encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding composition, or by another cell. "Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses contact of an agent capable of modulating FDF03 activity to a human or animal subject, a cell, tissue, physiological compartment, or physiological fluid. "Treatment of a cell" also encompasses situations where the FDF03 inhibitory receptor agonist or FDF03 bisepcific agent contacts the appropriate FDF03 receptor or receptors, e.g., in the fluid phase or colloidal phase, as well as situations where the agonist or antagonist contacts a fluid, e.g., where the fluid is in contact with a cell or receptor, but where it has not been demonstrated that the agonist or antagonist contacts the cell or receptor.

As used herein, the term "agent" includes compounds that modulate, e.g., up-modulate or stimulate and down-modulate or inhibit, the expression and/or activity of a molecule of the invention. As used herein the term "inhibitor" or "inhibitory agent" includes agents which inhibit the expression and/or activity of a molecule of the invention.

"Inhibitors" and "antagonists" or "activators" and "agonists" refer to inhibitory or activating molecules, respectively, e.g., for the activation of, e.g., a ligand, receptor, cofactor, gene, cell, tissue, or organ. A modulator of, e.g., a gene, a receptor, a ligand, or a cell, is a molecule that alters an activity of the gene, receptor, ligand, or cell, where activity can be activated, inhibited, or altered in its regulatory properties. The modulator may act alone, or it may use a cofactor, e.g., a protein, metal ion, or small molecule Inhibitors are compounds that decrease, block, prevent, delay activation, inactivate, desensitize, or down regulate, e.g., a gene, protein, ligand, receptor, or cell. Activators are compounds that increase, activate, facilitate, enhance activation, sensitize, or up regulate, e.g., a gene, protein, ligand, receptor, or cell. An inhibitor may also be defined as a composition that reduces, blocks, or inactivates a constitutive activity. An "agonist" is a compound that interacts with a target to cause or promote an increase in the activation of the target. Agonists also includes activation of a subset of functions, i.e., a "partial agonist". An "antagonist" is a compound that opposes the actions of an agonist. An antagonist prevents, reduces, inhibits, or neutralizes the activity of an agonist. An antagonist can also prevent, inhibit, or reduce constitutive activity of a target, e.g., a target receptor, even where there is no identified agonist.

As used herein, the term "antibody" refers to an isolated or recombinant binding agent that comprises the necessary variable region sequences to specifically bind an antigenic epitope. Therefore, an antibody is any form of antibody or fragment thereof that exhibits the desired biological activity, e.g., binding the specific target antigen. Thus, it is used in the broadest sense and specifically covers monoclonal antibodies (including full length monoclonal antibodies), polyclonal antibodies, human antibodies, humanized antibodies, chimeric antibodies, nanobodies, diabodies, multispecific antibodies (e.g., bispecific antibodies), and antibody fragments including but not limited to scFv, Fab, and $Fab_2$, so long as they exhibit the desired biological activity.

As used herein, the phrase "antibody fragment thereof" or "antigen binding fragment thereof" when used with respect to an antibody encompasses a fragment or a derivative of an antibody that substantially retains its biological activity. Therefore, an antibody fragment is a portion of a full length antibody and generally includes the antigen binding or variable region thereof. Examples of antibody fragments include Fab, Fab', $F(ab')_2$, and Fv fragments; diabodies; linear antibodies; single-chain antibody molecules, e.g., sc-Fv; and multispecific antibodies formed from antibody fragments. Typically, an antibody fragment or derivative retains at least 50% of its biological activity. Preferably, an antibody fragment or derivative retains at least 60%, 70%, 80%, 90%, 95%, 99% or 100% of its biological activity. An antibody fragment can include conservative amino acid substitutions that do not substantially alter its biologic activity.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope (or ligand). In contrast, conventional (polyclonal) antibody preparations typically include a multitude of antibodies directed against (or specific for) different epitopes. The term monoclonal indicates that the antibody is obtained from a substantially homogeneous population of antibodies, and is not to be construed as requiring production of the antibody by any particular method. For example, monoclonal antibodies useful with the present invention may be made by the hybridoma method first described by Kohler et al., Nature 256: 495 (1975), or may be made by recombinant DNA methods (see, e.g., U.S. Pat. No. 4,816,567). Useful monoclonal antibodies may also be isolated from phage antibody libraries using, for example, the techniques described in Clackson et al., Nature 352: 624-628 (1991) and Marks et al., J. Mol. Biol. 222: 581-597 (1991).

The monoclonal antibodies referred to herein include chimeric antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA 81: 6851-6855 (1984)).

As used herein, the term "carcinogenesis" refers to the development of a malignant or neoplastic cell or tumor.

As used herein, the term "cell-mediated response" refers to a host response to an antigen, cell, or organism mediated by T cells as well as nonspecific cells of the immune system including but not limited to NK cells, macrophages, neutrophils, eosinophils, and basophils.

"Effective amount" encompasses an amount sufficient to ameliorate or prevent a symptom or sign of the medical condition. Effective amount also means an amount sufficient to allow or facilitate diagnosis. An effective amount for a particular patient or veterinary subject may vary depending on factors such as the condition being treated, the overall health of the patient, the method route and dose of administration and the severity of side affects (see, e.g., U.S. Pat. No. 5,888,530 issued to Netti, et al.). An effective amount can be the maximal dose or dosing protocol that avoids significant side effects or toxic effects. The effect will result in an improvement of a diagnostic measure or parameter by at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%, where 100% is defined as the diagnostic parameter shown by a normal subject (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

As used herein, the term "FDF03 inhibitory receptor" encompasses all forms of FDF03 inhibitory receptor protein regardless of the source including but not limited to FDF03 inhibitory as disclosed in the commonly owned WO 98/24906. "FDF03 activating receptor" encompasses all forms of FDF03 activating receptor protein regardless of the source including but not limited to FDF03 activating receptor as disclosed in the commonly owned WO 2000/040721. Unless specifically distinguished, "FDF03" can refer to both receptors As used herein, the term "metastatic tumor" refers to a tumor cell that grows at a site distant from the primary tumor. "Metastatic burden" refers to the quantitation of metastatic tumors.

As used herein, the term "peptide" includes relatively short chains of amino acids linked by peptide bonds. The term "peptidomimetic" includes compounds containing non-peptidic structural elements that are capable of mimicking or antagonizing peptides.

As used herein, the term "primary tumor" refers to a tumor that remains in situ.

"Small molecules" are provided for the treatment of physiology and disorders of tumors and cancers. "Small molecule" is defined as a molecule with a molecular weight that is less than 10 kD, typically less than 2 kD, and preferably less than 1 kD. Small molecules include, but are not limited to, inorganic molecules, organic molecules, organic molecules containing an inorganic component, molecules comprising a radioactive atom, synthetic molecules, peptide mimetics, and antibody mimetics. As a therapeutic, a small molecule may be more permeable to cells, less susceptible to degradation, and less apt to elicit an immune response than large molecules. Small molecules, such as peptide mimetics of antibodies and cytokines, as well as small molecule toxins are described (see, e.g., Casset, et al. (2003) *Biochem. Biophys. Res. Commun.* 307:198-205; Muyldermans (2001) *J. Biotechnol.* 74:277-302; Li (2000) *Nat. Biotechnol.* 18:1251-1256; Apostolopoulos, et al. (2002) *Curr. Med. Chem.* 9:411-420; Monfardini, et al. (2002) *Curr. Pharm. Des.* 8:2185-2199; Domingues, et al. (1999) *Nat. Struct. Biol.* 6:652-656; Sato and Sone (2003) *Biochem. J.* 371:603-608; U.S. Pat. No. 6,326,482 issued to Stewart, et al).

As used herein the term "subject" refers to any living organisms in which an immune response can be elicited, preferably the subjects are mammals. Exemplary subjects include, but are not limited to humans, monkeys, dogs, cats, mice, rats, cows, horses, goats and sheep.

As used herein, the term "T cell", or "T lymphocyte" is refers to any cells within the T cell lineage from a mammal, e.g., human. Preferably, T cells are progenitor or effector T cells that express either CD4 and/or CD8, and a tumor-specific T cell receptor. The various T cell populations described herein can be defined based on their cytokine profiles and their function as is known in the art.

As used herein, the term "treat" refers to the application or administration of a therapeutic agent to a subject, or application or administration of a therapeutic agent to an isolated tissue or cell line from a subject, who has a disease or disorder, a symptom of disease or disorder or a predisposition toward a disease or disorder, with the purpose of curing, healing, alleviating, relieving, altering, remedying, ameliorating, improving or affecting the disease or disorder.

As used herein, the term "tumor" refers to any malignant or neoplastic cell.

B. Modulation of Cellular Responses

Featured herein is a method for stimulating or augmenting a cell-mediated response to a tumor in a subject, comprising administering to a subject in need thereof an agent that agonizes the biological activity of the FDF03 inhibitory receptor or binds to both the inhibitory and activating FDF03 receptors. Also featured herein is a method of increasing cellular cytotoxicity against a target, comprising administering to a cell an effective amount of an agent that modulates FDF03 activity, wherein the FDF03 inhibitory receptor activity is enhanced. Also, featured herein is a method of mitigating the immune-suppressive environment induced by tumor microenvironments.

Any cell-mediated response where FDF03 expressing cells participate can be stimulated or augmented using the disclosed methods. Such cell-mediated responses encompass innate immune cell responses. Cell-mediated responses can be measured by routine methods used in the art. See, e.g., Coligan et al., eds., CURRENT PROTOCOLS IN IMMUNOLOGY (John Wiley & Sons, current edition).

In particular, the manipulation of FDF03 activity can result in an increase of cellular cytotoxicity against a target. Any cytotoxic cell (or cytotoxic cell progenitor) that expresses FDF03, interacts with its target through a FDF03-mediated interaction, or whose differentiation and/or stimulation into a cytotoxic effector cell involves FDF03 can be modulated by this method. Such cells include but are not limited to NK cells, Tregs, NKT cells, CD4+ T cells, CD8+ T cells, macrophages, dendritic cells, neutrophils, and mast cells. Cellular cytotoxicity can be assessed by any suitable method. Exemplary methods include examining release of radiolabel from labeled target cells, e.g., $^{51}$Cr, colorimetric assays, e.g., Cyto-Tox96® non-radioactive assay (Promega), granzyme release assays, lactate dehydrogenase assays, and bioluminescence cytotoxicity assays (e.g., Biovision Research Products (Mountain View, Calif.)). Furthermore, FDF03 agonists may induce enhanced induction of T cells, NK cells, NKT cells or B cells, by inducing innate myeloid lineage cells to express molecules that activate said cells during the antigen presentation process or anti-tumor effector phase; that is to say indirect activation of effector cells of the adaptive immunity.

Any suitable target cell can be a target for the cell-mediated response, particularly the cytotoxic, response of the present invention. Preferably, the target is mammalian. The target can be syngeneic, allogeneic, or xenogeneic to the responding cell. In most embodiments, the target is syngeneic or allogeneic. In a preferred embodiment, the target is syngeneic to the responding effector cell. The target cell can be a normal or abnormal cell. Exemplary cells include a tumor cell, a virally infected cell, and a cell expressing FDF03 ligand by recombinant means. Thus, target cells include but are not limited to established cell lines such as CT-26 or 4T1 cells, short term cell lines, or cells isolated from a sample taken from a subject, e.g., dissociated tumor cells. In cells which express FDF03 or a FDF03 ligand, the expression can be naturally occurring or by recombinant means using method known in the art. See, e.g., CURRENT PROTOCOLS IN MOLECULAR BIOLOGY (John Wiley & Sons, most recent edition).

In some embodiments, the tumor target or other cellular target expresses a ligand for FDF03. Sometimes, the FDF03 ligand (or FDF03 associated ligand) is CD99

In one embodiment, the agent of the present method is an agonist FDF03 specific antibody or a biologically active fragment thereof. The agonist antibody will recognize the inhibitory FDF03 receptor. Additionally a bispecific antibody recognizing both the inhibitory and activating forms of FDF03 is useful. Exemplary antibodies include a bispecific FDF03 antibody and an agonist antibody specific for FDF03 inhibitory receptor. The bispecific antibody can be an antibody that naturally cross reacts with both receptors, or an genetically engineered antibody. The antibodies can be generated in cell culture, in phage, or in various animals, including but not limited to cows, rabbits, goats, mice, rats, hamsters, guinea pigs, sheep, dogs, cats, monkeys, chimpanzees, apes. Therefore, the antibody useful in the present methods is typically a mammalian antibody. Phage techniques can be used to isolate an initial antibody or to generate variants with altered specificity or avidity characteristics. Such techniques are routine and well known in the art. In one embodiment, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one $V_L$ and one $V_H$ region in the host cell. Exemplary descriptions of recombinant means of antibody generation and production include Delves, ANTIBODY PRODUCTION: ESSENTIAL TECHNIQUES (Wiley, 1997); Shephard, et al., MONOCLONAL ANTIBODIES (Oxford University Press, 2000); and Goding, MONOCLONAL ANTIBODIES: PRINCIPLES AND PRACTICE (Academic Press, 1993).

The antibody useful in the present methods can be modified by recombinant means to increase greater efficacy of the antibody in mediating a desired function such as increased half-life. See, e.g., Borrebaeck (ed.) ANTIBODY ENGINEERING (Oxford University Press, 1995). For example, antibodies can be modified by substitutions using recombinant means. Typically, the substitutions will be conservative substitutions. For example, at least one amino acid in the constant region of the antibody can be replaced with a different residue. See, e.g., U.S. Pat. No. 5,624,821, U.S. Pat. No. 6,194,551, Application No. WO99/58572; and Angal, et al., *Mol. Immunol.* 30:105-08 (1993). The modification in amino acids includes deletions, additions, and substitutions of amino acids. The antibodies can also be fusion proteins where the antibody or biologically active fragment thereof is joined to another biologically relevant agent, e.g., a cytokine, an adhesion molecule, a costimulatory molecule, and the like as well as biologically relevant portions of such molecules.

In some embodiments, the agent useful in this method is a FDF03 inhibitory receptor-specific antibody, an FDF03 bispecific antibody, or biologically active fragment thereof. Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang, et al. (1999) *J. Biol. Chem.* 274:27371-27378; Baca, et al. (1997) *J. Biol. Chem.* 272:10678-10684; Chothia, et al. (1989) *Nature* 342:877-883; Foote and Winter (1992) *J. Mol. Biol.* 224:487-499; U.S. Pat. No. 6,329,511 issued to Vasquez, et al.).

Purification of antigen is not necessary for the generation of antibodies. Immunization can be performed by DNA vector immunization, see, e.g., Wang, et al. (1997) *Virology* 228: 278-284. Alternatively, animals can be immunized with cells bearing the antigen of interest. Splenocytes can then be isolated from the immunized animals, and the splenocytes can fused with a myeloma cell line to produce a hybridoma (Meyaard, et al. (1997) *Immunity* 7:283-290; Wright, et al. (2000) *Immunity* 13:233-242; Preston, et al. (1997) *Eur. J. Immunol.* 27:1911-1918). Resultant hybridomas can be screened for production of the desired antibody by functional assays or biological assays, that is, assays not dependent on possession of the purified antigen. Immunization with cells may prove superior for antibody generation than immunization with purified antigen (Kaithamana, et al. (1999) *J. Immunol.* 163:5157-5164).

Antibody to antigen and ligand to receptor binding properties can be measured, e.g., by surface plasmon resonance (Karlsson, et al. (1991) *J. Immunol. Methods* 145:229-240; Neri, et al. (1997) *Nat. Biotechnol.* 15:1271-1275; Jonsson, et al. (1991) *Biotechniques* 11:620-627) or by competition ELISA (Friguet, et al. (1985) *J. Immunol. Methods* 77:305-319; Hubble (1997) *Immunol. Today* 18:305-306). Antibodies can be used for affinity purification to isolate the antibody's target antigen and associated bound proteins, see, e.g., Wilchek, et al. (1984) *Meth. Enzymol.* 104:3-55.

Antibodies will usually bind with at least a $K_D$ of about $10^{-3}$ M, more usually at least $10^{-6}$ M, typically at least $10^{-7}$ M, more typically at least $10^{-8}$ M, preferably at least about $10^{-9}$ M, and more preferably at least $10^{-10}$ M, and most preferably at least $10^{-11}$ M (see, e.g., Presta, et al. (2001) *Thromb. Haemost.* 85:379-389; Yang, et al. (2001) *Crit. Rev. Oncol. Hematol.* 38:17-23; Carnahan, et al. (2003) *Clin. Cancer Res.* (Suppl.) 9:3982s-3990s).

In some embodiments, the subject has cancer and can be treated with the agent of the present invention as described below.

C. Methods of Treatment Using FDF03 Inhibitory Agents

Featured herein is a method of preventing or treating cancer, comprising administering to a subject in need thereof an effective amount of an agent that stimulates FDF03 inhibitory receptor biological activity. In some embodiments, the cancer is skin cancer.

The subject treated by the present methods includes a subject having an adenocarcinoma, leukemia, lymphoma, melanoma, sarcoma, or teratocarcinoma. The tumor can be a cancer of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. Such tumors include, but are not limited to: neoplasma of the central nervous system: glioblastomamultiforme, astrocytoma, oligodendroglial tumors, ependymal and choroids plexus tumors, pineal tumors, neuronal tumors, medulloblastoma, schwannoma, meningioma, meningeal sarcoma: neoplasma of the eye: basal cell carcinoma, squamous cell carcinoma, melanoma, rhabdomyosarcoma, retinoblastoma; neoplasma of the endocrine glands: pituitary neoplasms, neoplasms of the thyroid, neoplasms of the adrenal cortex, neoplasms of the neuroendocrine system, neoplasms of the gastroenteropancreatic endocrine system, neoplasms of the gonads; neoplasms of the head and neck: head and neck cancer, oral cavity, pharynx, larynx, odontogenic tumors: neoplasms of the thorax: large cell lung carcinoma, small cell lung carcinoma, non-small cell lung carcinoma, neoplasms of the thorax, malignant mesothelioma, thymomas, primary germ cell tumors of the thorax; neoplasms of the alimentary canal: neoplasms of the esophagus, neoplasms of the stomach, neoplasms of the liver, neoplasms of the gallbladder, neoplasms of the exocrine pancreas, neoplasms of the small intestine, vermiform appendix and peritoneum, adenocarcinoma of the colon and rectum, neoplasms of the anus; neoplasms of the genitourinary tract: renal cell carcinoma, neoplasms of the renal pelvis and ureter, neoplasms of the bladder, neoplasms of the urethra, neoplasms of the prostate, neoplasms of the penis, neoplasms of the testis; neoplasms of the female reproductive organs: neoplasms of the vulva and vagina, neoplasms of the cervix, adenocarcinoma of the uterine corpus, ovarian cancer, gynecologic sarcomas; neoplasms of the breast; neoplasms of the skin: basal cell carcinoma, squamous carcinoma, dermatofibrosarcoma, Merkel cell tumor; malignant melanoma; neoplasms of the bone and soft tissue: osteogenic sarcoma, malignant fibrous histiocytoma, chrondrosarcoma, Ewing's sarcoma, primitive neuroectodermal tumor, angiosarcoma; neoplasms of the hematopoietic system: myelodysplastic syndromes, acute myeloid leukemia, chronic myeloid leukemia, acute lymphocytic leukemia, HTLV-1, and T-cell leukemia/lymphoma, chronic lymphocytic leukemia, hairy cell leukemia, Hodgkin's disease, non-Hodgkin's lymphomas, mast cell leukemia; neoplasms of children: acute lymphoblastic leukemia, acute myelocytic leukemias, neuroblastoma, bone tumors, rhabdomyosarcoma, lymphomas, renal and liver tumors.

Any subject can be treated with the methods and compositions provided herein. Such a subject is a mammal, preferably a human, in need of such treatment. Veterinary uses of the disclosed methods and compositions are also contemplated. Such uses would include prevention of carcinogenesis, treatment of cancer, and prevention and treatment of autoimmune diseases in domestic animals, livestock and thoroughbred horses.

Various pharmaceutical compositions and techniques for their preparation and use will be known to those of skill in the art in light of the present disclosure. For a detailed listing of suitable pharmacological compositions and associated administrative techniques one may refer to the detailed teachings herein, which may be further supplemented by texts such as REMINGTON: THE SCIENCE AND PRACTICE OF PHARMACY 20th Ed. (Lippincott, Williams & Wilkins 2003.

The formulation and delivery methods will generally be adapted according to the site and the disease to be treated. Exemplary formulations include, but are not limited to, those suitable for parenteral administration, e.g., intravenous, intraarterial, intramuscular, or subcutaneous administration, including formulations encapsulated in micelles, liposomes or drug-release capsules (active agents incorporated within a biocompatible coating designed for slow-release); ingestible formulations; formulations for topical use, such as creams, ointments and gels; and other formulations such as inhalants, aerosols and sprays. The dosage of the compounds of the invention will vary according to the extent and severity of the need for treatment, the activity of the administered composition, the general health of the subject, and other considerations well known to the skilled artisan.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds exhibiting high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition, age, weight, and therapeutic responsiveness. Dosage amount and interval may be adjusted individually to provide plasma levels of the active moiety sufficient to maintain the desired therapeutic effects, or minimal effective concentration (MEC). The MEC will vary for each compound but can be estimated from in vitro data; for example, the concentration necessary to achieve 50-90% stimulation of FDF03 inhibitory receptor biological activity.

The mode of administration is not particularly important. In one embodiment, the mode of administration is an I.V. bolus. In another embodiment, the administration is topical. Alternately, one may administer the compound in a local rather than systemic manner, for example, via injection of the compound directly into a tumor or autoimmune lesion, often in a depot or sustained release formulation.

The modulatory agents of the invention can be administered alone or in combination with one or more additional agents. For example, in one embodiment, two or more agents described herein can be administered to a subject. In another embodiment, an agent described herein can be administered in combination with other immunomodulating agents. Examples of other immunomodulating reagents include antibodies that block a costimulatory signal, (e.g., against CD28, ICOS), antibodies that activate an inhibitory signal via CTLA4, and/or antibodies against other immune cell markers (e.g., against CD40, against CD40 ligand, or against cytokines), fusion proteins (e.g., CTLA4-Fc, PD-1-Fc), and immunosuppressive drugs, (e.g., rapamycin, cyclosporine A or FK506). Yet more examples of immunomodulatory reagents include agonists of toll-like receptors (TLRs) (e.g., CpG ODN oligos). In certain instances, it may be desirable to further administer other agents that upregulate immune responses, for example, agents which deliver T cell activation signals, in order elicit or augment an immune response. Such agents include, but are not limited to the co-administration of cytokines such as IL-2, IL-10, IFN-α and IFN-γ. Also contemplated are cytokine antagonists, such as anti-IL-10.

D. Therapeutic Compositions, Methods

The present invention provides FDF03 antibodies for use, e.g., in the treatment of proliferative conditions and disorders, including cancer, tumors, angiogenesis, cachexia, cancer cachexia, anorexia, and pre-cancerous disorders, e.g., dysplasia.

To prepare pharmaceutical or sterile compositions including an agonist of FDF03 inhibitory receptor, the cytokine analogue or mutein, antibody thereto, or nucleic acid thereof, is admixed with a pharmaceutically acceptable carrier or excipient, see, e.g., *Remington's Pharmaceutical Sciences and U.S. Pharmacopeia: National Formulary*, Mack Publishing Company, Easton, Pa. (1984). Formulations of therapeutic and diagnostic agents may be prepared by mixing with physiologically acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.).

The route of administration is by, e.g., topical or cutaneous application, subcutaneous injection, injection or infusion by intravenous, intraperitoneal, intracerebral, intramuscular, intraocular, intraarterial, intracerebrospinal, intralesional, or pulmonary routes, or by sustained release systems or an implant. Gene transfer vectors, e.g., for the central nervous system, have been described (see, e.g., Cua, et al. (2001) *J. Immunol.* 166:602-608; Sidman et al. (1983) *Biopolymers* 22:547-556; Langer, et al. (1981) *J. Biomed. Mater. Res.* 15:167-277; Langer (1982) *Chem. Tech.* 12:98-105; Epstein, et al. (1985) *Proc. Natl. Acad. Sci. USA* 82:3688-3692; Hwang, et al. (1980) *Proc. Natl. Acad. Sci. USA* 77:4030-4034; U.S. Pat. Nos. 6,350,466 and 6,316,024).

Selecting an administration regimen for a therapeutic depends on several factors, including the serum or tissue turnover rate of the entity, the level of symptoms, the immunogenicity of the entity, and the accessibility of the target cells in the biological matrix. Preferably, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med.* 348: 601-608; Milgrom, et al. (1999) *New Engl. J. Med.* 341:1966-1973; Slamon, et al. (2001) *New Engl. J. Med.* 344:783-792; Beniaminovitz, et al. (2000) *New Engl. J. Med.* 342:613-619; Ghosh, et al. (2003) *New Engl. J. Med.* 348:24-32; Lipsky, et al. (2000) *New Engl. J. Med.* 343:1594-1602).

Antibodies, antibody fragments, and cytokines can be provided by continuous infusion, or by doses at intervals of, e.g., one day, one week, or 1-7 times per week. Doses may be provided intravenously, subcutaneously, topically, orally, nasally, rectally, intramuscular, intracerebrally, intraspinally, or by inhalation. A preferred dose protocol is one involving the maximal dose or dose frequency that avoids significant undesirable side effects. A total weekly dose is generally at least 0.05 µg/kg body weight, more generally at least 0.2 µg/kg, most generally at least 0.5 µg/kg, typically at least 1 µg/kg, more typically at least 10 µg/kg, most typically at least 100 µg/kg, preferably at least 0.2 mg/kg, more preferably at least 1.0 mg/kg, most preferably at least 2.0 mg/kg, optimally at least 10 mg/kg, more optimally at least 25 mg/kg, and most optimally at least 50 mg/kg (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:133-144). The desired dose of a small molecule therapeutic, e.g., a peptide mimetic, natural product, or organic chemical, is about the same as for an antibody or polypeptide, on a moles/kg basis.

An effective amount for a particular patient may vary depending on factors such as the condition being treated, the overall health of the patient, the method route and dose of administration and the severity of side affects (see, e.g., Maynard, et al. (1996) *A Handbook of SOPs for Good Clinical Practice*, Interpharm Press, Boca Raton, Fla.; Dent (2001) *Good Laboratory and Good Clinical Practice*, Urch Publ., London, UK).

Typical veterinary, experimental, or research subjects include monkeys, dogs, cats, rats, mice, rabbits, guinea pigs, horses, and humans.

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is derived from the same species as the animal targeted for treatment, thereby minimizing a humoral response to the reagent.

Methods for co-administration or treatment with a second therapeutic agent, e.g., a cytokine, steroid, chemotherapeutic agent, antibiotic, or radiation, are well known in the art (see, e.g., Hardman, et al. (eds.) (2001) *Goodman and Gilman's The Pharmacological Basis of Therapeutics*, 10$^{th}$ ed., McGraw-Hill, New York, N.Y.; Poole and Peterson (eds.) (2001) *Pharmacotherapeutics for Advanced Practice:A Practical Approach*, Lippincott, Williams & Wilkins, Phila., PA; Chabner and Longo (eds.) (2001) *Cancer Chemotherapy and Biotherapy*, Lippincott, Williams & Wilkins, Phila., PA).

An effective amount of therapeutic will decrease the symptoms typically by at least 10%; usually by at least 20%; preferably at least about 30%; more preferably at least 40%, and most preferably by at least 50%.

E. Kits and Diagnostic Reagents

This invention provides FDF03 proteins, fragments thereof, nucleic acids, and fragments thereof, in a diagnostic kit. Also provided are binding compositions, including antibodies or antibody fragments, for the detection of FDF03, and metabolites and breakdown products thereof. Typically, the kit will have a compartment containing either a FDF03 polypeptide, or an antigenic fragment thereof, a binding composition thereto, or a nucleic acid, e.g., a nucleic acid probe or primer. The nucleic acid probe or primer specifically hybridizes under stringent conditions to a nucleic acid encoding either the activating or inhibitory form of FDF03.

The kit can comprise, e.g., a reagent and a compartment, a reagent and instructions for use, or a reagent with a compartment and instructions for use. The reagent can comprise FDF03 proteins or antigenic fragments thereof, a binding composition, or a nucleic acid. A kit for determining the binding of a test compound, e.g., acquired from a biological sample or from a chemical library, can comprise a control compound, a labeled compound, and a method for separating free labeled compound from bound labeled compound.

Diagnostic assays can be used with biological matrices such as live cells, cell extracts, cell lysates, fixed cells, cell cultures, bodily fluids, or forensic samples. Conjugated antibodies useful for diagnostic or kit purposes, include antibodies coupled to dyes, isotopes, enzymes, and metals (see, e.g., Le Doussal, et al. (1991) *New Engl. J. Med.* 146:169-175; Gibellini, et al. (1998) *J. Immunol.* 160:3891-3898; Hsing and Bishop (1999) *New Engl. J. Med.* 162:2804-2811; Everts, et al. (2002) *New Engl. J. Med.* 168:883-889). Various assay formats exist, such as radioimmunoassays (RIA), ELISA, and lab on a chip (U.S. Pat. Nos. 6,176,962 and 6,517,234).

This invention provides polypeptides and nucleic acids of FDF03 receptors, fragments thereof, in a diagnostic kit, e.g., for the diagnosis of proliferative conditions, cancer, tumors, and precancerous disorders, e.g., dysplasia.

Also provided are binding compositions, including antibodies or antibody fragments, for the detection of FDF03 receptors and metabolites and breakdown products thereof. Typically, the kit will have a compartment containing either an FDF03 inhibitory receptor or FDF03 activating receptor polypeptide, or an antigenic fragment thereof, a binding composition thereto, or a nucleic acid, such as a nucleic acid probe, primer, or molecular beacon (see, e.g., Rajendran, et al. (2003) *Nucleic Acids Res.* 31:5700-5713; Cockerill (2003) *Arch. Pathol. Lab. Med.* 127:1112-1120; Zammatteo, et al. (2002) *Biotech. Annu. Rev.* 8:85-101; Klein (2002) *Trends Mol. Med.* 8:257-260).

A method of diagnosis can comprise contacting a sample from a subject, e.g., a test subject, with a binding composition that specifically binds to FDF03 inhibitory receptor or a bispecific binding composition that binds to both the inhibitory receptor or the activating receptor. The method can further comprise contacting a sample from a control subject, normal subject, or normal tissue or fluid from the test subject, with the binding composition. Moreover, the method can additionally comprise comparing the specific binding of the composition to the test subject with the specific binding of the composition to the normal subject, control subject, or normal tissue or fluid from the test subject. Expression or activity of a test sample or test subject can be compared with that from a control sample or control subject. A control sample can comprise, e.g., a sample of non-affected or non-inflamed tissue in a patient suffering from an immune disorder. Expression or activity from a control subject or control sample can be provided as a predetermined value, e.g., acquired from a statistically appropriate group of control subjects.

The broad scope of this invention is best understood with reference to the following examples, which are not intended to limit the inventions to the specific embodiments.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

EXAMPLES

I. General Methods

Standard methods in molecular biology are described (Maniatis, et al. (1982) *Molecular Cloning, A Laboratory Manual*, Cold Spring Harbor Laboratory Press, Cold Spring Harbor, N.Y.; Sambrook and Russell (2001) *Molecular Cloning*, 3$^{rd}$ ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies is described (Coligan, et al. (2001) *Current Protcols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protcols in Immunology*, Vol. 4, John Wiley, Inc., New York).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry*, 2$^{nd}$ ed.; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Methods for the treatment and diagnosis of cancer are described (see, e.g., Alison (ed.) (2001) *The Cancer Handbook*, Grove's Dictionaries, Inc., St. Louis, Mo.; Oldham (ed.) (1998) *Principles of Cancer Biotherapy*, 3$^{rd}$. ed., Kluwer Academic Publ., Hingham, Mass.; Thompson, et al. (eds.) (2001) *Textbook of Melanoma*, Martin Dunitz, Ltd., London, UK; Devita, et al. (eds.) (2001) *Cancer: Principles and Practice of Oncology*, 6th ed., Lippincott, Phila, Pa.; Holland, et al. (eds.) (2000) *Holland-Frei Cancer Medicine*, B C Decker, Phila., PA; Garrett and Sell (eds.) (1995) *Cellular Cancer Markers*, Humana Press, Totowa, N.J.; MacKie (1996) *Skin Cancer*, 2$^{nd}$ ed., Mosby, St. Louis; Moertel (1994) *New Engl. J. Med.* 330:1136-1142; Engleman (2003) *Semin. Oncol.* 30(3 Suppl. 8):23-29; Mohr, et al. (2003) *Onkologie* 26:227-233).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

II. Generation of FDF03 Receptor Antibodies

The FDF03 activating receptor-Ig fusion protein was constructed consisting of the extracellular domain of mouse FDF03 activating receptor fused to the Fc portion of human IgG1. The extracellular residues (corresponding to amino acids 29-192, see, e.g., GenBank Accession No. Q9UKJ0) was subcloned in the Xho1 site of a modified pCDM8.1 g expression plasmid (E. E Bates et. al. (1998) *Mol. Immunol.* 35:513) to produce the plasmid LL1091. LL1091 was transiently expressed in 293T cells to produce soluble FDF03 activating receptor-Ig fusion protein. Lewis rats were immunized with the fusion protein. Hybridoma fusions were screened by ELISA against the immunizing FDF03 activating receptor-Ig fusion protein, and an irrelevant human Ig fusion protein as a negative control.

32 antibody producing hybridomas were selected and antibodies were further screened on a mouse mast cell degranulation assay. Anti-FDF03 mAb induced degranulation of the activating FDF03 transfected mast cell line DT865. Titrations of anti-FDF03 antibodies were made in a 96-well flat-bottom plate in 50 ul assay media (RPMI, 1% BSA, 25 mM Hepes). Mouse mast cells expressing the mouse FDF03 activating receptor (DT865) were spun down and resuspended at $2 \times 10^6/$ ml, 100 ul/well was added to the antibody titrations. Cells were cultured at 37°, 5% $CO_2$ for 1 hr. At the end of the stimulation period, 20 ul was removed from each well and transfered to 60 ul 1.3 mg/ml B-hexosaminidase substrate (4-NitrophenyN-acetyl-b-D-glucosaminide, Sigma N9376). Supernatant/substrate reaction proceeded for 3.5 hr, 37° C. Reaction was stopped by the addition of 0.2M glycine, pH 10.7 and OD405-570 was measured to assess the extent of degranulation.

The FDF03 inhibitory receptor-Ig fusion protein consisted of the extracellular domain of the mouse FDF03 inhibitory receptor fused to the Fc portion of human IgG1. The extracellular residues (corresponding to amino acids 29-200; see, e.g., GenBank Accession No. NP_038467) was subcloned in the Xho1 site of a modified pCDM8.1 g expression plasmid (E. E Bates et. al. supra) to produce the plasmid LL1090. LL1090 was transiently expressed in 293T cells to produce soluble FDF03 inhibitory receptor-Ig. Lewis rats were immunized with three KLH conjugated peptides (Invitrogen), and the mouse FDF03 inhibitory receptor-Ig protein. Fusion screened by ELISA against the immunizing fusion protein and an irrelevant human Ig fusion protein as a negative control.

Titrations of anti-mouse FDF03 inhibitory receptor antibodies were made in a 96-well flat-bottom plate in 50 ul assay media (RPMI, 1% BSA, 25 mM Hepes). Mouse mast cells expressing the mouse FDF03 inhibitory receptor (DT866) were spun down and resuspended at $2 \times 10^6$/ml, 100 ul/well was added to the antibody titrations. The stimulating anti-CD200R antibody, DX87 was then added in 50 ul/well so that the final concentration was 1 ug/ml. Cells were cultured at 37°, 5% $CO_2$ for 30 min. Wells were washed 2x. Goat anti mouse Ig was added as a cross linking reagent at 10 ug/ml. Cells were cultured at 37°, 5% $CO_2$ for 1 hr. At the end of the stimulation period, 20 ul was removed from each well and transferred to 60 ul 1.3 mg/ml β-hexosaminidase substrate (4-NitrophenyN-acetyl-b-D-glucosaminide, Sigma N9376). Supernatant/substrate reaction proceeded for 3.5 hr, 37° C. Reaction was stopped by the addition of 0.2M glycine, pH 10.7 and OD405-570 was measured to assess the extent of inhibition of CD200R induced degranulation.

III. FDF03 (DX173) Treatment in 4T1 Tumor Model

DX173 antibody recognizes both activating and inhibitory murine FDF03 receptors. Rat anti-human IL-4 mAb (25D2) was used as a control Plated 4T1 tumor cells were trypsinized (TrypLE) and washed 2 times in PBS (45 mls) to remove FBS. Cells were then resuspended in PBS at a concentration of $1.0 \times 10^6$ cells/ml and placed on ice. Mice were injected subcutaneously with 200 µL ($2.0 \times 10^5$ cells). Injection was done in the left flank 1.5 CM caudal from the knee & ~0.5 CM ventral from the knee.

At day 7 post tumor implant, animals were randomly assigned into 3 groups based on visual assessment of tumor size (n=8 per group), as described in Table 1. On day 7 post tumor implant, animals also received subcutaneous injection (in 2504 volume) of either PBS (buffer control), 1 mg of IgG1 isotype mAb (PAB557) (Ab control), or 1 mg of anti-FDF03 bispecific mAb (DX173). Animals were treated 3 times per week with this regimen for 3 weeks.

TABLE 1

| Group | Species | Number of mice | Treatment | Dose/Route | Schedule |
|---|---|---|---|---|---|
| 1 | BALB/c AnN | 8 | Tumor: PBS (diluent) | 1 mg/SQ | starting -d7 SQ 3x/wk |
| 2 | BALB/c AnN | 8 | Tumor: 1 mg IgG1 control Ab (25D2-PAB557A) | 1 mg/SQ | starting -d7 SQ 3x/wk |
| 3 | BALB/cAnN | 8 | Tumor: 1 mg FDF03 (DX173) | 1 mg/SQ | starting -d7 SQ 3x/wk |

Tumor sizes were measured with Vernier calipers in three dimensions (width and length and height) and tumor volume were calculated using the formula: $4/3\pi(1/2)(w/2)(h/2)$ where l, w, and h represent length, width, and height respectively. Tumors were measured periodically to evaluate the effects of treatment on tumor growth. Statistical analysis was done using t-test. The last 2 measurements (days 25 and 28) included 6 animals each for the PBS and isotype treatments and 5 animals for the DX173 treatment (rest of the animals were used for myeloid cell analysis). To measure lung metastasis, lung tissues were fixed in 10% buffered formalin. The number of pulmonary metastatic lesions on lung surfaces were quantified under a dissecting microscope.

Figure 2:
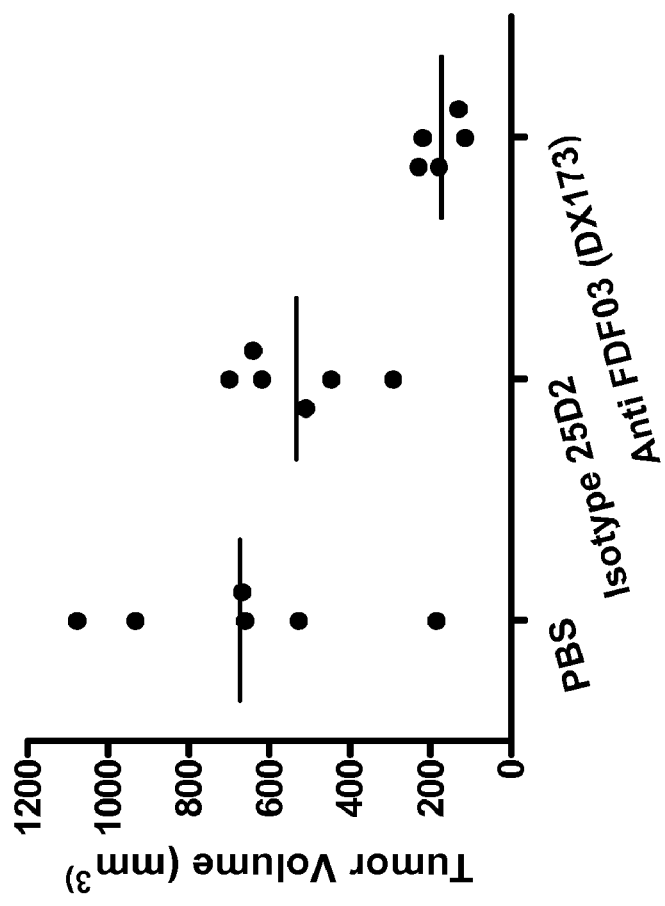
FIG. 2 shows inhibition of 4T1 mammary carcinoma tumorigenesis upon treatment with DX173.
Figure 3:
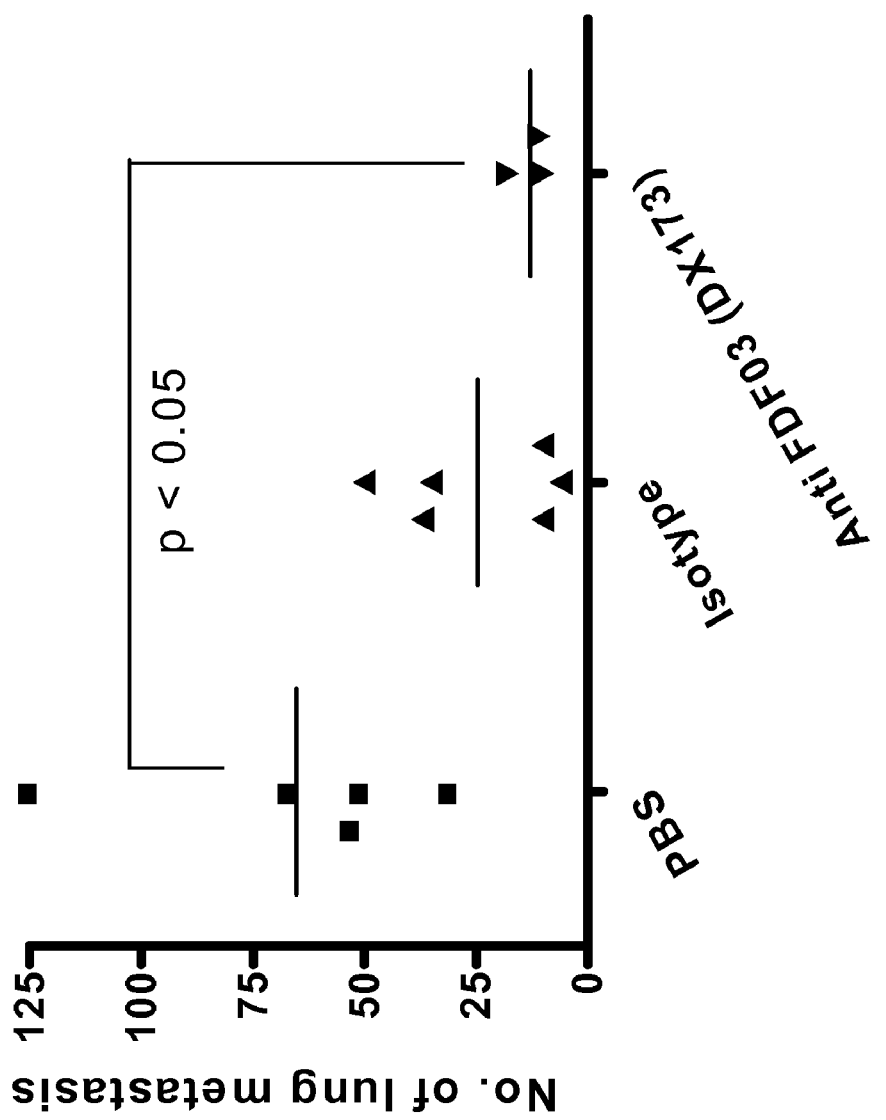
FIG. 3 shows a decrease in 4T1 mammary carcinoma metastatic burden upon treatment with DX173.

FIGS. 1 and 2 show that the bispecific DX173 antibody was able to inhibit or reduce tumor growth in a statistically significant manner. FIG. 3 shows DX173 was able to reduce 4T1 tumor-induced lung metastasis.

IV. FDF03 (DX276 and DX173) Treatment in CT26 Tumor Model

The DX276 Ab recognizes inhibitory FDF03 and the DX173 Ab recognizes both activating and inhibitory FDF03. Plated CT26 tumor cells were trypsinized (TrypLE) and washed 2 times in PBS (45 mls) to remove FBS. Cells were then resuspended in PBS at a concentration of $1.0 \times 10^6$ cells/ml and placed on ice. Mice were injected subcutaneously with 200 µL ($2.0 \times 10^5$ cells). Injection was done in the left flank 1.5 CM caudal from the knee and ~0.5 CM ventral from the knee. At day 7 post tumor implant, animals were randomly assigned into 4 groups based on visual assessment of tumor size (n=6 per group) as described in Table 2. On day 8 post tumor implant, animals also received subcutaneous injection (in 2504 volume) of either PBS (buffer control), 1 mg of IgG1 isotype mAb (PAB557) (Ab control), 1 mg of anti-FDF03 bispecific mAb (DX173), or 1 mg of anti-FDF03 inhibitory mAb (DX276). Animals were treated 3 times per week with this regimen for 3 weeks (9 total treatments).

TABLE 2

| Group | Species | N (mice) | Treatment | Dose/Route | Schedule |
|---|---|---|---|---|---|
| 1 | BALB/cAnN | 6 | Tumor: PBS (diluent) | 1 mg/SQ | starting -d8 SQ 3x/wk |
| 2 | BALB/cAnN | 6 | Tumor: 1 mg IgG1 control Ab (25D2-PAB557A) | 1 mg/SQ | starting -d8 SQ 3x/wk |
| 3 | BALB/cAnN | 6 | Tumor: 1 mg FDF03 (DX173) | 1 mg/SQ | starting -d8 SQ 3x/wk |

TABLE 2-continued

| Group | Species | N (mice) | Treatment | Dose/Route | Schedule |
|---|---|---|---|---|---|
| 4 | BALB/cAnN | 6 | Tumor: 1 mg FDF03 (DX276) | 1 mg/SQ | starting -d8 SQ 3x/wk |

Tumor sizes were measured with Vernier calipers in three dimensions (width and length and height) and tumor volume were calculated using the formula: $4/3\pi(l/2)(w/2)(h/2)$ where l, w, and h represent length, width, and height respectively. Tumors were measured periodically to evaluate the effects of treatment on tumor growth.

Figure 4:
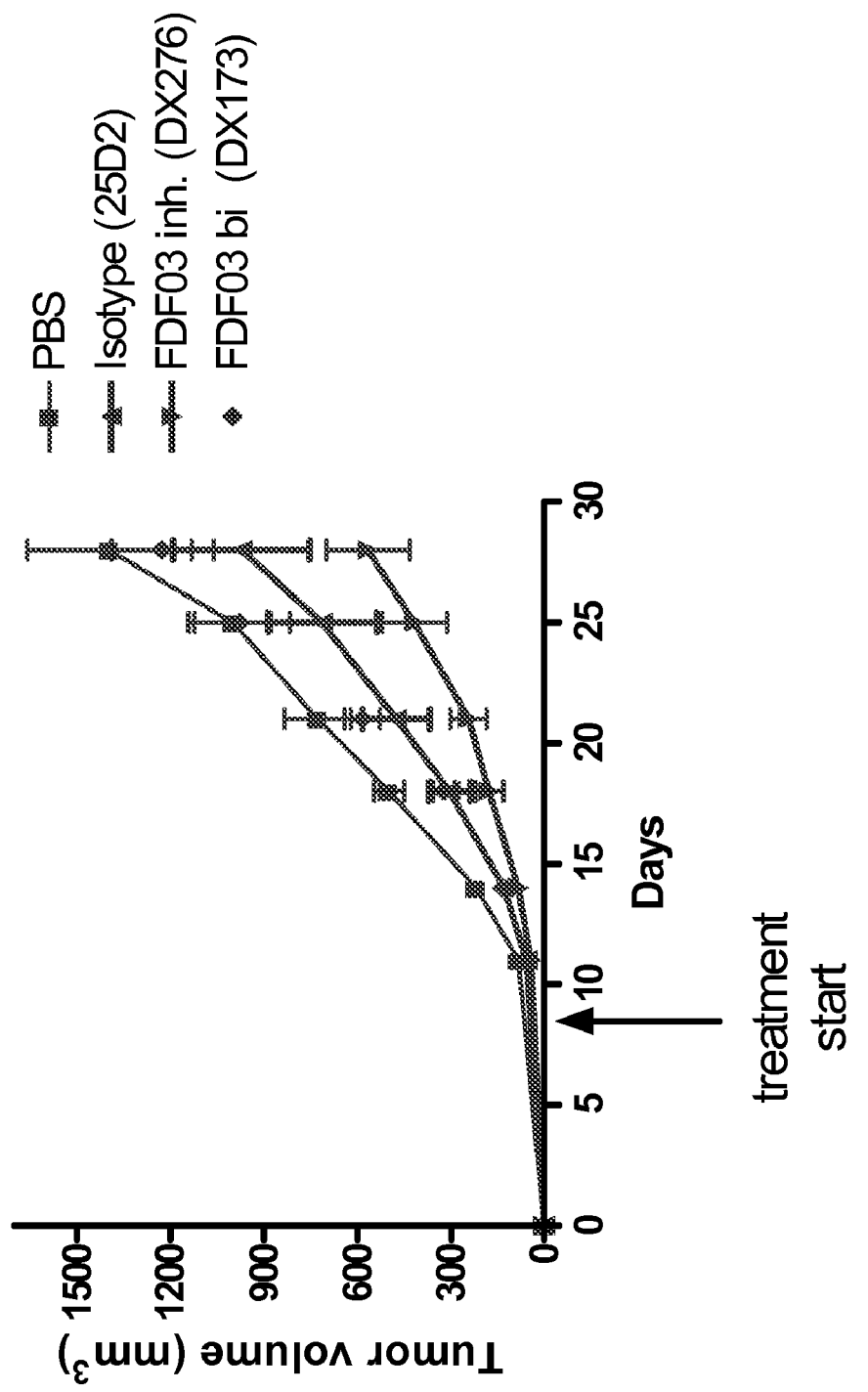
FIG. 4 shows inhibition of CT-26 colon carcinoma tumor growth upon treatment with DX276 (agonist antibody that binds to FDF03 inhibitory receptor) antibodies.
Figure 5:
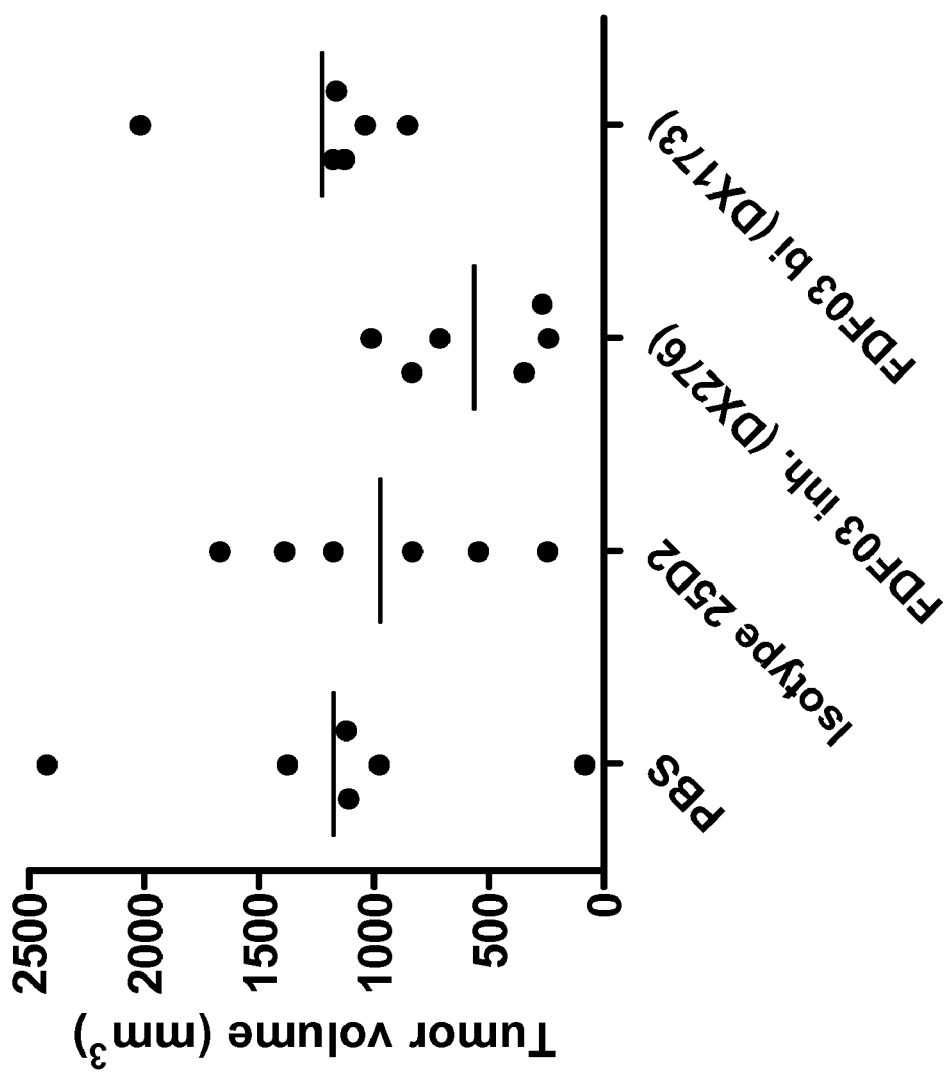
FIG. 5 shows inhibition of CT-26 colon carcinoma tumorigenesis upon treatment with DX276.

FIGS. 4 and 5 show that the agonist mAb specific for the inhibitory form of FDF03 (DX276) had the highest level of inhibition of tumor growth and tumorigenesis.

What is claimed is:

1. A method for inhibiting tumor growth in a subject having colon cancer, comprising administering to the subject an effective amount of an agonist antibody or partial-agonist antibody or antibody fragment thereof specific for the FDF03 inhibitory receptor.

2. The method of claim 1, wherein the antibody is a humanized, fully human or chimeric antibody.

3. The method of claim 1, wherein the tumor is a primary or a metastatic tumor.

4. The method of claim 1, wherein the subject is a human.

5. A method for reducing metastatic burden in a subject having colon cancer, comprising administering to the subject an effective amount of an agonist antibody or partial-agonist antibody, or antibody fragment thereof specific for the FDF03 inhibitory receptor.

6. The method of claim 5, wherein the antibody is a humanized, fully human or chimeric antibody.

7. The method of claim 5, wherein the subject is a human.

8. A method for inhibiting tumor growth in a subject having breast cancer, comprising administering to the subject an effective amount of an antibody or antibody fragment thereof that binds to the FDF03 inhibitory receptor and to the FDF03 activating receptor.

9. The method of claim 8, wherein the antibody is a humanized, fully human or chimeric antibody.

10. The method of claim 8, wherein the tumor is a primary or a metastatic tumor.

11. The method of claim 8, wherein the subject is a human.

12. A method for reducing metastatic burden in a subject having breast cancer, comprising administering to the subject an effective amount of an antibody or antibody fragment thereof that binds to the FDF03 inhibiting receptor and to the FDF03 activating receptor.

13. The method of claim 12, wherein the antibody is a humanized, fully human or chimeric antibody.

14. The method of claim 12, wherein the subject is a human.

* * * * *